United States Patent [19]

Takeda et al.

[11] Patent Number: 5,464,516
[45] Date of Patent: Nov. 7, 1995

[54] PROCESS FOR PRODUCING AN ELECTROPHORESIS SEPARATION LAYER

[75] Inventors: Hisao Takeda, Kenagawa; Youichi Koshiji, Kanagawa; Hidehiro Kubota, Kanagawa; Takashi Iizuka, Kanagawa, all of Japan

[73] Assignees: Hymo Corporation; Atto Corporation, both of Tokyo, Japan

[21] Appl. No.: 235,934

[22] Filed: May 2, 1994

Related U.S. Application Data

[63] Continuation-in-part of Ser. No. 868,439, Apr. 15, 1992, abandoned.
[51] Int. Cl.$^6$ .................... C25B 9/00; H01B 1/00
[52] U.S. Cl. .................... 204/182.9; 204/182.8; 252/500; 524/827; 428/474.4; 428/327
[58] Field of Search .................... 252/500, 512, 252/518; 524/827; 204/182.8, 182.9; 428/474.4, 327

[56] References Cited

U.S. PATENT DOCUMENTS

| | | | |
|---|---|---|---|
| 3,948,743 | 4/1976 | Monthony et al. | 204/180 G |
| 4,737,258 | 4/1988 | Ogawa et al. | 204/182.8 |

FOREIGN PATENT DOCUMENTS

| | | |
|---|---|---|
| 61-28512 | 2/1986 | Japan . |
| 62-91850 | 4/1987 | Japan . |
| 502456 | 9/1988 | Japan . |
| 210654 | 9/1988 | Japan . |
| 263548 | 10/1989 | Japan . |
| 302153 | 12/1989 | Japan . |
| 222555 | 1/1990 | Japan . |
| 4184163 | 11/1990 | Japan . |
| 8704948 | 8/1987 | WIPO . |
| 9204625 | 3/1992 | WIPO . |

*Primary Examiner*—Paul Lieberman
*Assistant Examiner*—M. Kopec
*Attorney, Agent, or Firm*—Browdy and Neimark

[57] ABSTRACT

An electrophoresis separation layer is produced which comprises a polyacrylamide gel which remains stable even when stored for a long time and is available for analyzing substances of an extremely wide molecular weight range in electrophoresis for determining molecular weight. The electrophoresis separation layer of the present invention includes a polyacrylamide gel with an aqueous solution containing an amine of a specific pH value, an ampholyte and an acid at a specific ratio as an electrolytic solution in the gel. This separation layer can be produced by lowering the pH value of the electrolytic solution in the polyacrylamide gel to such an extent as not to cause any hydrolysis of amide while achieving a suitable potential gradient distribution in the gel during the electrophoresis.

9 Claims, No Drawings

PROCESS FOR PRODUCING AN ELECTROPHORESIS SEPARATION LAYER

The present invention is a continuation in part of Serial No. 07/868,439, filed Apr. 15, 1992, now abandoned, the entire contents of which are hereby incorporated by reference.

FIELD OF THE INVENTION

The present invention relates to a process for producing an electrophoresis separation layer comprising a polyacrylamide gel. The separation layer is used in the fields of biochemistry and medicine for separating and analyzing substances of biological origin, such as proteins and nucleic acids.

DESCRIPTION OF THE PRIOR ART

Paper, agarose and starch have been used as gel matrices in electrophoresis. However, the gel matrices have poor separating power and thus give only unclear bands In recent years, polyacrylamide gels have been used in electrophoresis. It is expected that excellent separation can be achieved by virtue of a highly accurate molecular sieve effect.

In particular, an electrophoretic method using a crosslinked polyacrylamide gel containing an electrolytic solution is currently used in electrophoretic analysis, since the pore size of the gel can be arbitrarily controlled by varying the concentration of the acrylamide and the composition of the crosslinking agent. A gel suitable for each purpose intended may be prepared, depending upon the molecular weight of the substance to be separated, such as a protein or a nucleic acid. In general, a polyacrylamide gel of relatively high concentration may be used for separating proteins and nucleic acids of relatively low molecular weights, while a polyacrylamide gel of a low concentration may be used for separating proteins and nucleic acids of relatively high molecular weights. These techniques are disclosed in, for example, Japanese Laid-open Patents Nos. 5202456/1988, 91850/1987 and 22555/1990.

Japanese Laid-Open Patent No. 502456/1988 discloses a method for supplying a buffer solution in an electrophoresis separation process. In this method, an electrode solution, which is generally used in the form of a liquid, is formulated into a gel so as to facilitate the contact of the same with a gel to be used for separation. Namely, a buffer solution is supplied in horizontal electrophoresis with the use of a supportive matrix in the form of a gel plate. Two electrode buffer solutions are respectively incorporated in one gel piece. These gel pieces are then contacted with the supportive matrix in a manner such that the matrix between the gel pieces provides the available separation region. The gel pieces comprise agarose or polyacrylamide. The content of the electrode buffer in each gel piece ranges from 80 to 99% by weight.

Japanese Laid-open Patent No. 91850/1987 discloses a method for producing a medium for aqueous polyacrylamide gel electrophoresis. This method relates to crosslinking polymerization of an acrylamide monomer in the presence of a crosslinking agent, water and a polymerization initiating means wherein the polymerization initiating means consists of a combination of a peroxide, a photosensitizer and excited light and does not contain any reductant.

Japanese Laid-open Patent No. 22555/1990 discloses an electrophoresis gel medium kit which is used to form a polyacrylamide gel medium.

Techniques have also been proposed relating to gradient gels, in which the concentration of acrylamide is continuously varied against the direction of electrophoresis so as to separate proteins or nucleic acids having a wide molecular weight distributions, as shown in Japanese Laid-open Patents Nos. 28512/1986, 210654/1988 and 263548/1989.

Japanese Laid-open Patent No. 28512/1986 discloses a method for producing an electrophoresis gel material. In this method, polymerization is initiated in a homogeneous photopolymerization system in which a water soluble organic initiator is used, or in a heterogeneous photopolymerization system in which an organic initiator is suspended or dispersed in an aqueous photopolymerization solution so as to produce a gradient gel having a continuous pore size gradient.

Japanese Laid-open Patent No. 210654/1988 and No. 263548/1989 disclose media for electrophoresis. Each of these patents provides a gel medium having an improved aqueous polyacrylamide gel concentration gradient and a substantially equal, excellent separation performance in both a lower molecular weight region and a high molecular weight region.

Furthermore, Japanese Laid-open Patent No. 302153/1989 discloses a technique for producing a gel for electrophoresis in which the acrylamide concentration is varied stepwise. In this method, aqueous solutions of monomers, differing in acrylamide concentration from each other, are successively laminated followed by polymerization, thus giving a gel for electrophoresis.

In these known techniques, the concentration of polyacrylamide constituting a gel practically ranges from 4 to 20% by weight. When the acrylamide concentration is lower than 4% by weight, sufficient gel strength cannot be obtained. When the acrylamide concentration exceeds 20% by weight, on the other hand, the gel obtained is liable to be peeled from the inner wall of a container.

Further, it is possible to separate proteins based on only a molecular weight difference between them by treating them with sodium dodecyl sulfate (hereinafter referred to as SDS) so as to render uniform the changes of the protein molecules before conducting the electrophoresis. Laemmli's formulation, in which tri-(hydroxymethyl)aminomethane (hereinafter referred to as tris) partially neutralized by hydrochloric acid is used as the gel buffer solution, and tris glycine salt is used as the electrophoresis electrode solution, is advantageously used for protein analysis [cf. U.K. Laemmli, *Nature*, 227, 680 (1970)]. In the gel electrolytic solution to be used in this Laemmli's formulation, approximately 10 to 20% by mole of tris is neutralized so as to attain a pH value of 8.8.

As described above, the pH value of the electrolytic solution contained in the polyacrylamide gel to be used in Laemmli's formulation is 8.8 and amide groups are hydrolyzed with the lapse of time. The hydrolysis may proceed even at a low temperature, for example, in a refrigerator, and the polyacrylamide gel comes to have anionic groups in part. As a result the electrophoretic distance of a protein is shortened and its electrophoretic pattern becomes vague. When the percentage neutralization of tris is elevated and the pH value of the gel electrolytic solution is adjusted to a neutral level or lower in order to prevent the hydrolysis, the performance of separating the proteins according to the difference in molecular weight is deteriorated and the polyacrylamide gel is not available in practice any more.

Further, the molecular weight range of proteins which can be analyzed with the use of a polyacrylamide gel of an acrylamide concentration of from 4 to 20% by weight, namely, a practically usable acrylamide concentration range as described above, is restricted. When Laemmli's electrolytic solution is used, gels of acrylamide concentrations of 4% by weight and 20% by weight are available for separating, respectively, protein molecules of 500,000 and 20,000 molecular weight at the most. Thus, there has been an urgent requirement further to widen the measurable molecular weight range.

SUMMARY OF THE INVENTION

It is an object of the present invention to solve the above-mentioned problems by providing a process for producing an electrophoresis separation layer comprising a polyacrylamide gel which remains stable even when stored for a long time and is available for analyzing substances of an extremely wide molecular weight range in electrophoresis for determining molecular weight.

In order to achieve the above-mentioned object, the electrophoresis separation layer of the present invention comprises an aqueous solution containing an amine of a specific pH value, an ampholyte and an acid at a specific ratio as an electrolytic solution in the polyacrylamide gel.

Thus, an electrophoresis separation layer is provided for determining the molecular weights of a wide range of substances. This separation layer can be produced by lowering the pH value of the electrolytic solution in the polyacrylamide gel to such as extent as not to cause any hydrolysis of amide while achieving a suitable potential gradient distribution in the gel during the electrophoresis.

More specifically, the present invention aims to provide a process for producing an electrophoretic separation layer comprising a polyacrylamide gel in combination with an aqueous solution containing an amine and an ampholyte as the electrode solution, in which the electrolytic solution in the gel is an aqueous solution containing an acid, an amine and an ampholyte. The ratio of the amine to the acid contained in the electrolytic solution ranges from 1:0.6 to 1:1 part by gram equivalent; the ratio of the acid to the ampholyte contained therein ranges from 1:0.5 to 1:4 parts by gram equivalent; the pKa value of the ampholyte ranges from 7 to 11, the pKa value of the amine ranges from 8 to 8.5, and the pKa value of the acid is 5 or below.

In the process for producing an electrophoresis separation layer according to the present invention, it is preferable that both the amine in the electrophoresis electrode solution and the amine in the electrolytic solution of the gel be tris(hydroxymethyl)aminomethane.

In the process for producing an electrophoresis separation layer according to the present invention, the pH values of the electrolytic solution in the gel range from about 4 to about 7.5.

In the process for producing an electrophoresis separation layer according to the present invention, it is preferable that the electrophoresis electrode solution of the cathode side contain 0.01% by weight or more of a salt of dodecyl sulfate.

In a process for conducting electrophoresis of a protein, using the electrophoresis separation layer according to the present invention, it is preferable to use add dodecyl sulfate ions to the protein during the electrophoresis.

In the electrophoresis separation layer according to the present invention, the pKa value of the ampholyte contained in the electrolysis solution in the polyacrylamide gel is the same as and/or lower than the pKa value of the ampholyte contained in the electrophoresis electrode solution of the cathode side.

In the electrophoresis separation layer according to the present invention, each of the ampholytes used in the electrode solution and in the electrolytic solution in the gel has anionic groups and cationic groups of the same number in a single molecule.

In the process for producing an electrophoresis separation layer according to the present invention, it is preferred that the ampholyte to be used in the electrode solution of the cathode side be one selected from among glycine, serine, asparagine, β-alanine, N-tris(hydroxymethyl)methyl-3-aminopropanesulfonic acid and N-tris(hydroxymethyl)methylglycine.

In the process for producing an electrophoresis separation layer according to the present invention, it is preferred that the ampholyte to be used in the electrode solution of the cathode side by glycine or N-tris(hydroxymethyl)methylglycine.

In the process for producing an electrophoresis separation layer according to the present invention, it is preferred that the ampholyte to be used in the electrolytic solution in the gel be one selected from the group consisting of glycine, serine, asparagine, β-alanine, N-tris(hydroxymethyl)methyl-3-aminopropanesulfonic acid, N-tris(hydroxymethyl)methyl-2-aminoethane-sulfonic acid and mixtures thereof.

In the process for producing an electrophoresis separation layer according to the present invention, it is particularly preferred that the acid to be used in the electrolytic solution in the gel be selected from the group consisting of hydrochloric acid, acetic acid and mixtures thereof.

Further, the present invention relates to a process for producing an electrophoresis separation layer comprising polymerizing acrylamide in the presence of a crosslinking agent, water, an electrolytic solution for the gel and a polymerization initiating means thereby to produce a polyacrylamide gel. The electrolytic solution for the gel comprises an aqueous solution containing an acid, an amine and an ampholyte. The ratio of the amine to the acid contained in the electrolytic solution ranges from 1:0.6 to about 1:1 part by gram equivalent, and the ratio of the acid to the ampholyte contained therein ranges from about 1:0.5 to about 11:4 parts by gram equivalent.

In the process for producing an electrophoresis separation layer according to the present invention, 1 to 10% by weight, based upon the total monomers, of a divinyl compound is copolymerized with the acrylamide. It is preferred that the divinyl compound be N,N-methylenebisacrylamide.

The polymerization initiation means preferably comprises a redox type initiator. The preferred polymerization initiation means comprises a polymerization catalyst comprising a peroxide and N,N,N',N'-tetramethylethylenediamine.

DETAILED DESCRIPTION OF THE PREFERRED EMBODIMENT

In the process for producing an electrophoresis separation layer of the present invention, it is desirable that the acid constituting the electrolytic solution of the gel, which lowers the pH value of the electrolytic solution, be added in such amount as not to cause hydrolysis of amide groups. Preferably, the acid should also have a large dissociation constant and a pKa value of about 5 or less. Particularly preferable examples of such acids include hydrochloric acid and monobasic water soluble organic acids.

The ampholyte used in the electrophoresis separation layer has the same number of anionic groups and cationic groups in each molecule. At a pH value somewhat lower than the pKa value, all of the anionic groups and all of the cationic groups dissociate, thus achieving an electrically neutral state. At a pH value somewhat higher than the pKa value, on the other hand, only the anionic groups dissociate while the dissociation of the cationic groups is suppressed. Thus, the ampholyte is negatively charged in this case.

Accordingly, the above-mentioned ampholyte acts substantially as a monobasic weak. Thus, the part by gram equivalent given above as its content is calculated as a monobasic weak acid. The pKa value is generally measured at 20° C. An ampholyte which has a pKa value of 11 or more does not contribute to the reduction in potential gradient, while an ampholyte having a pKa value or 7 or less effuses together with leading ions (acid radicals having a pKa value of 5 or less contained in the electrolytic solution in the gel).

Examples of ampholytes to be used in the present invention include glycine, serine, asparagine, β-alanine, N-tris(hydroxymethyl)methyl-3-aminopropanesulfonic acid (hereinafter referred to simply as TAPS), N-tris(hydroxymethyl)methylglycine (hereinafter referred to as tricine) and N-tris(hydroxymethyl)methyl-2-aminoethanesulfonic acid (hereinafter referred to as TES).

The pKa value of the ampholyte constituting the electrolytic solution in the gel must not exceed that of the ampholyte constituting the electrode solution of the cathode side. Further, the pKa value of the ampholyte participating in the reduction of the electric potential gradient must be the same as or lower than that of the ampholyte migrating from the electrode solution toward the gel, i.e., trailing ions. Either one or more substances may be selected, depending on the purpose, as the ampholyte constituting the electrolytic solution in the gel. When two or more ampholytes are used, they successively migrate toward the anode side in their order of pKa and, as a result, the potential gradient in the gel is gradually changed. Thus, the range of molecular weight to be determined can be increased, similar to the case in which the acrylamide concentration is varied.

The polyacrylamide gel which is used in the electrophoresis separation layer of the present invention can be produced by any conventional method. However, the pH value of the electrolytic solution in the gel is controlled, and ampholytes are added thereto. For example, N,N-methylenebisacrylamide (hereinafter referred to as BIS) is most commonly employed as a water soluble divinyl compound for crosslinking. Other ordinary divinyl compounds such as N,N-diallyltartramide may also be used in the present invention. The divinyl compound is copolymerized at a ratio of from about 1 to about 10% by weight based on the total monomers.

In order to impart elasticity to the gel and to improve its brittleness, the aqueous monomer solution may further contain water-soluble polymer such as agarose, polyacrylamide, polyvinyl alcohol, polyvinylpyrrolidone, polyethylene oxide or polymethyl vinyl ether. Alternatively, 20% by weight or less of a nonionic monovinyl monomer, other than acrylamide, may be copolymerized therewith.

The polymerization of the monomers may be performed with the use of an initiator or a radical formed by UV radiation. It is preferred to use a redox type initiator, which comprises a combination of a peroxide such as ammonium persulfate (hereinafter referred to as APS) with a reductant such as N,N,N',N'-tetramethylethylenediamine (hereinafter referred to as TEMED), as the initiator, although the invention is nor restricted thereto. The above-mentioned peroxide and reductant are used in an amount of from about 0.05 to about 5% by weight based upon the total monomers. The polymerization temperature is not particularly restricted, as long as the initiator can exert its function. It is usually preferable to perform the polymerization at from about 15 to about 50° C.

In the separation layer for electrophoresis according to the present invention, anions migrate toward the anode side when the electricity is turned on. More specifically, anions in the cathodic electrode solution migrate into the gel, while anions in the gel migrate into the anodic electrode solution.

When an aqueous solution of a strong acid salt is used as the electrolytic solution of the gel and an aqueous solution of a weak acid salt is used as the electrode solution, as in the case of the above-mentioned Laemmli's formulation, strong acid radicals in the gel migrate toward the anode side while weak acid radicals in the cathodic electrode solution migrate into the gel. When a weak base, such as tris, is used as to supply cations common to the electrolytic solution of the gel and the electrode solution, some of the weak acid salt molecules lose their charge, and the amount of ions is thus decreased. As a result, the electric resistance (i.e, potential gradient) in the gel is elevated and the rate of electrophoretic separation of protein molecules is increased.

Thus, the tris-strong acid salt part in the electrophoretic gel is clearly distinguished from the tris-weak acid salt part therein, and a change in the potential gradient around the boundary becomes marked with an increase in the percentage neutralization of tris due to the strong acid. When the percentage neutralization ratio is high, therefore, substances to be separated are liable to be concentrated around the boundary, which interferes with the separability of, in particular, low molecular weight fractions. In order to prevent this phenomenon, it is necessary to lower the electric resistance of the weak acid salt part in the gel appropriately.

When a weak acid is previously added to the electrolytic solution of the gel, as in the process of the present invention, the amount of ions of the weak acid salt part is increased and, as a result, the electric resistance is lowered. Thus, the electric resistance may be arbitrarily varied by controlling the pKa value and concentration of the weak acid. In the presence of strong acid radicals, furthermore, the pH value is low and thus the weak acid is electrically neutral, so that it is unnecessary to lower the electric resistance.

However, the pKa values of weak acids suitable for controlling the electric resistance range from about 7 to about 11, considerably differing from the dissociation constants of common anionic groups.

In the present invention, therefor, an ampholyte having cationic groups and anionic groups in the same number is used as a pseudo-weak acid so as to control the pKa value of cationic groups within the range as specified above. Thus, the dissociation of cationic groups is suppressed in the alkaline side and the ampholyte acts as an anion. In acidic side, on the other hand, the same number of cationic groups and anionic groups dissociate and therefore, the ampholyte is electrically neutral and thus does not contribute to electric conduction.

Thus, the potential gradient distribution in the gel during electrophoresis can be controlled by initially adding an appropriate amount of an ampholyte having a suitable pKa value to the electrolytic solution of the gel. Therefore, electrophoretic patterns of high resolution of various samples differing in molecular weight from each other can be obtained over a wide range.

When an ampholyte is added to the electrolytic solution of the gel, as in the process of the present invention, staining of proteins with an acidic dye after completion of electrophoresis can be facilitated. This might be because the dissociation of anionic groups in the ampholyte is suppressed during staining under acidic conditions from acetic acid, and the ampholyte acts as cations which prevent interference from anionic substances bound to proteins during the staining.

Laemmli's standard formulation, in which the percentage neutralization of tris from an acid in the electrolytic solution in the gel is low, suffers from a decrease in mobility due to the high pH value when stored for a long time. As a result, the separation power of the gel deteriorates. When the percentage neutralization of the electrolytic solution of the gel is elevated to attain a neutral pH level or less, no deterioration is observed even after a prolonged storage. In this case, however, the mobility is largely increased as compared with the Laemmli's standard formulation.

In contrast, when an ampholyte is added to the electrolytic solution in the gel, as in the case of the process for producing a polyacrylamide gel for electrophoresis of the present invention, an electrophoretic pattern comparable to those obtained by using the Laemmli's standard formulation can be obtained even when the percentage by neutralization is elevated in order to prevent the deterioration. The presence or absence of the ampholyte in the electrolytic solution of the gel does not affect the electrophoresis, so long as the electrode solution contains SDS.

In addition, the polyacrylamide gel obtained by the process of the present invention, which contains ampholytes differing in pKa value from each other in the gel, is effective in separating samples having a wide molecular weight distribution range, and thus an electrophoretic pattern comparable to the one obtained using a gradient gel can be obtained, even through the polyacrylamide gel in the separation layer is a uniform gel having an acrylamide concentration of 10%.

Additionally, use of the separation layer of the present invention makes it possible to easily separate polypeptides having a molecular weight as low as 20,000 or less which can barely be separated by the conventional methods. Furthermore, the presence of the ampholyte facilitates staining proteins after completion of the electrophoresis.

SPECIFIC EXAMPLES

Example 1

A spacer of 1 mm thickness was sandwiched between a rectangular glass sheet (12 cm in width, 10 cm in length) and another glass sheet of the same size having a concavity at the upper side, thus preparing a glass plate. A monomer solution comprising 12.5% acrylamide, 2.6% BIS and each electrolytic solution composition listed in Table 1 was mixed with 400 ppm of APS and 400 ppm of TEMED. The mixture as obtained was poured into the plate and polymerized in the conventional manner. Thus a separation layer for electrophoresis was prepared.

Commercially available proteins of known molecular weights were subjected to electrophoresis using the above-mentioned separation layer, and the migration distances were measured.

Each marker protein was treated with β-mercaptoethanol and SDS and 7% glycerol and 0.05% bromphenol blue (hereinafter refereed to as BPB) were added thereto prior to conducting the test.

The electrode solution was Laemmli's formulation comprising 0.025 mol/L of tris, 0.192 mol/L if glycine and 0.1% by weight of SDS.

Electrophoresis was conducted at a constant electric current of 20 mA. When the electrophoretic end of BPB reached 5 mm above the bottom, the electricity was turned off.

Staining was effected in a solution of 0.25% Comassie Brilliant Blue (hereinafter referred to as CBB) G-250, 10% acetic acid and 30% methanol for two hours. Decoloration was effected in a solution of 7% acetic acid and 3% methanol over day and night, while exchanging the solution occasionally.

The ratio of the electrophoretic distance of each protein to that of BPB was defined as the mobility. The results are shown in Tables 2 and 3.

Table 2 shows the mobilities immediately after production of the polyacrylamide gel, while Table 3 shows the data obtained after the polyacrylamide gel had been stored at 5° C. for days.

TABLE 1

Composition of Electrolytic Solution of Electrophoresis Gel

|  | Sample | Sample | Comp. Sample 1 | Comp. Sample 2 |
| --- | --- | --- | --- | --- |
| Tris (mol/l) | 0.094 | 0.094 | 0.094 | 0.375 |
| Hydrochloric acid (mol/l) | 0.080 | 0.080 | 0.080 | 0.060 |
| Glycine (mol/l) | 0.190 | 0.190 | — | — |
| SDS (wt %) | — | 0.1 | 0.1 | 0.1 |
| pH | 7.3 | 7.3 | 7.3 | 7.3 |

In the above table, samples 1 and 2 are expressed in mol/L. The ratio by gram equivalent of glycine to the acid (chloride ion) is as follows:

0.08:0.19=1:2.4.

TABLE 2

Mobility (immediately after production)

|  | Sample 1 | Sample 2 | Comp. Sample 1 | Comp. Sample 2 |
| --- | --- | --- | --- | --- |
| Protein mol. wt. $6.7 \times 10^4$ | 0.09 | 0.09 | 0.15 | 0.09 |
| Protein mol. wt. $3.0 \times 10^4$ | 0.35 | 0.35 | 0.48 | 0.39 |
| Protein mol. wt. $1.4 \times 10^4$ | 0.72 | 0.72 | 0.97 | 0.74 |

TABLE 3

Mobility (after storage at 5° C. for 120 days)

|  | Sample 1 | Sample 2 | Comp. Sample 1 | Comp. Sample 2 |
| --- | --- | --- | --- | --- |
| Protein mol. wt. $6.7 \times 10^4$ | 0.09 | 0.09 | 0.15 | 0.04 |
| Protein mol. wt. $3.0 \times 10^4$ | 0.35 | 0.35 | 0.48 | 0.11 |
| Protein mol. wt. $1.4 \times 10^4$ | 0.72 | 0.72 | 0.97 | 0.24 |

EXAMPLE 2

By using the same glass plate as the one used in Example 1, an electrophoretic separation layer was produced in accordance with each electrolytic solution composition listed in Table 4. Electrophoresis was then performed under the same conditions as those described in Example 1.

Table 5 shows the results of these electrophoresis separations in which BIS concentration was 5.0% in every case.

TABLE 4

Composition of Electrolytic Solution of Electrophoresis Gel

|  | Sample 3 | Sample 4 | Comp. Sample 3 | Comp. Sample 4 |
|---|---|---|---|---|
| Gel concentration (% T) | gradient 4–20 | 10 | gradient 4–20 | 10 |
| Tris (mol/l) | 0.094 | 0.094 | 0.375 | 0.094 |
| Hydrochloric acid (mol/l) | 0.086 | 0.086 | 0.060 | 0.086 |
| Glycine (mol/l) | 0.190 | 0.048 | — | — |
| Serine (mol/l) | — | 0.048 | — | — |
| TAPS (mol/l) | — | 0.048 | — | — |
| Tricine (mol/l) | — | 0.048 | — | — |
| SDS (wt. %) | 0.1 | 0.1 | 0.1 | 0.1 |
| pH | 7.0 | 7.1 | 8.8 | 7.0 |

TABLE 5

Mobility

|  | Sample 3 | Sample 4 | Comp. Sample 3 | Comp. Sample 4 |
|---|---|---|---|---|
| Protein mol. wt $9.4 \times 10^4$ | 0.17 | 0.17 | 0.17 | 0.25 |
| Protein mol. wt. $6.7 \times 10^4$ | 0.25 | 0.26 | 0.25 | 0.38 |
| Protein mol. wt. $4.3 \times 10^4$ | 0.35 | 0.35 | 0.35 | 0.65 |
| Protein mol. wt. $3.0 \times 10^4$ | 0.52 | 0.53 | 0.52 | 0.83 |
| Protein mol. wt. $2.0 \times 10^4$ | 0.69 | 0.72 | 0.70 | 0.96 |
| Protein mol. wt. $1.4 \times 10^4$ | 0.80 | 0.84 | 0.80 | 0.96 |

EXAMPLE 3

By using the same glass plate as the one used in Example 1, an electrophoretic separation layer was produced in accordance with each electrolytic solution composition listed in Table 6. This separation layer was then used to separate samples of low molecular weights. In each case, the BIS concentration was 5.0%.

Polypeptides manufactured by Pharmacia were used as molecular weight markers. Each marker was dissolved in an electrolytic solution of 50 mM tris hydrochloride (pH 6.8) containing 2.5% SDS and 5% β-mercaptoethanol. After 0.01% of CBB was added, the mixture was allowed to stand overnight at room temperature and then subjected to the test.

The electrode solution for electrophoresis containing 0,025 mol/L of tris and 0.1% by weight of SDS. Further, ampholytes for electrophoresis as specified in Table 6 were added thereto.

The electrophoresis was performed at a constant electric current of 20 mA. When the electrophoretic end of CBB reached 10 mm above the bottom, the electricity was turned off. After the electrophoresis was completed, the gel was fixed in a 50% methanol and a 10% acetic acid solution for 45 minutes. Staining was effected in a solution of 0,025% of CBBG-250 and 10% of acetic acid for two hours. Decoloration was effected in a solution of 10% acetic acid overnight while exchanging the solution at times.

The ratio of the electrophoretic distance of each protein to that of CBB was defined as the mobility. Table 7 shows the results.

TABLE 6

Composition of Electrolytic Solution of Electrophoresis Gel

|  | Sample 5 | Sample 6 | Sample 7 | Comp. Sample 6 |
|---|---|---|---|---|
| Gel conc. (% T) | 15 | 15 | 15 | 15 |
| Tris (mol/l) | 0.100 | 0.100 | 0.100 | 0.100 |
| Acid for neutralizing (mol/l) | HCl 0.082 | HCl 0.082 | HCl 0.092 | HCl 0.082 |
| Glycine (mol/l) | 0.048 | — | — | — |
| Serine (mol/l) | 0.048 | — | — | — |
| TAPS (mol/l) | 0.048 | — | — | — |
| Tricine (mol/l) | 0.048 | 0.100 | 0.100 | — |
| SDS (wt. %) | 0.1 | 0.1 | 0.1 | 0.1 |
| pH | 7.4 | 7.3 | 6.9 | 7.3 |
| Electrophoresis electrode sol. (mol/l) | TES 0.192 | Tricine 0.025 | Tricine 0.025 | Tricine 0.025 |

TABLE 7

Mobility

|  | Sample 5 | Sample 6 | Sample 7 | Comp. Sample 6 |
|---|---|---|---|---|
| Polypeptide mol. wt. $1.7 \times 10^4$ | 0.42 | 0.43 | 0.43 | 0.98 |
| Polypeptide mol. wt. $8.2 \times 10^3$ | 0.54 | 0.58 | 0.58 | 0.98 |
| Polypeptide mol. wt. $2.6 \times 10^3$ | 0.72 | 0.70 | 0.70 | 0.98 |

The foregoing description of the specific embodiments will so fully reveal the general nature of the invention that others can, by applying current knowledge, readily modify and/or adapt for various application such specific embodiments with out departing from the generic concept, and therefore such adaptations and modifications are intended to be comprehended within the meaning and range of equivalents of the disclosed embodiments. It is to be understood that the phraseology or terminology herein is for the purpose of description and not of limitation.

All references cited in this specification are hereby incorporated by reference.

What is claimed is:

1. A process for producing an electrophoresis separation layer consisting of a polyacrylamide gel and an electrolytic solution suitable for use in electrophoresis, wherein said electrolytic solution is an aqueous solution consisting essentially of an acid, amine and an ampholyte that has the same number of anionic groups and cationic groups in each single molecule as an electrophoresis cathodic electrode solution, which process consists essentially of:

polymerizing acrylamide in the presence of a crosslinking agent, water, an electrolytic solution for the polyacrylamide gel and a polymerization initiating means;

wherein the electrolytic solution in said polyacrylamide gel is an aqueous solution consisting essentially of an acid, an amine and an ampholyte, wherein the pH of the electrolytic solution in said polyacrylamide gel ranges from 4 to 7.5, said acid to be used in the electrolytic solution in the polyacrylamide gel is selected from the group consisting of monobasic acids and mixtures thereof, said ampholyte that is to be used for controlling the potential gradient of the electrolytic solution in the polyacrylamide gel satisfies the following characteristics (a) and (b):
  (a) the ampholyte has the same number of anionic groups and cationic groups in each single molecule, and
  (b) the ampholyte has a pKa value in the electrolytic solution in the polyacrylamide gel of no more than the pKa of the ampholyte in an electrophoresis electrode solution on the cathode side of the polyacrylamide gel, the ratio of the amine to the acid contained in the electrolytic solution in said polyacrylamide gel ranges from 1:0.6 to 1:1 part by gram equivalent; the ratio of the acid to the ampholyte contained therein ranges from 1:0.5 to 1:4 parts by gram equivalent; and the pKa value of said amine ranges from 8 to 8.5, the pKa value of said ampholyte ranges from 7 to 11, the pKa value of said acid is no more than 5; and connecting said electrophoresis separation layer to electrodes.

2. A process according to claim 1 wherein both the amine contained in the electrophoresis cathodic electrode solution and the amine contained in the electrolysis solution in said polyacrylamide gel are tris(hydroxymethyl)aminomethane.

3. A process according to claim 1 wherein said electrophoresis cathodic electrode solution contains a salt of dodecyl sulfate.

4. A process according to claim 1 wherein at least 0.1% of the salt of dodecyl sulfate is contained in the electrophoresis electrode solution of the cathode side.

5. A process according to claim 1 wherein said ampholyte to be used in the electrophoresis electrode solution of the cathode side is a compound selected from the group consisting of glycine, serine, asparagine, β-alanine, N-tris(hydroxymethyl)methylglycine and N-tris(hydroxymethyl)-methyl-3-aminopropanesulfonic acid.

6. A method according to claim 5 wherein said ampholyte to be used in the electrophoresis electrode solution of the cathode side is glycine.

7. A method according to claim 5 wherein the ampholyte to be used in he electrophoresis electrode solution of the cathode side is N-tris(hydroxymethyl)-methylglycine.

8. A process according to claim 1 wherein the ampholyte used in the electrolytic solution in the polyacrylamide gel controls the potential gradient.

9. A process according to claim 1 wherein the acid to be used in the electrolytic solution in the polyacrylamide gel is selected from the group consisting of hydrochloric acid, acetic acid and mixtures thereof.

* * * * *